(12) United States Patent
Peyman (10) Patent No.: US 10,736,571 B1
(45) Date of Patent: Aug. 11, 2020

(54) GLAUCOMA TESTING DEVICE AND A METHOD USING THE SAME

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 223 days.

(21) Appl. No.: 15/784,127

(22) Filed: Oct. 14, 2017

Related U.S. Application Data (60) Provisional application No. 62/408,653, filed on Oct. 14, 2016.

(51) Int. Cl.
| | |
|---|---|
| *A61B 5/1455* | (2006.01) |
| *A61B 3/16* | (2006.01) |
| *A61B 5/00* | (2006.01) |
| *A61B 5/145* | (2006.01) |
| *A61M 16/10* | (2006.01) |
| *A61M 16/00* | (2006.01) |
| *A61B 3/024* | (2006.01) |
| *A61B 3/10* | (2006.01) |
| *A61B 3/12* | (2006.01) |
| *A61B 5/0484* | (2006.01) |

(Continued)

(52) U.S. Cl.
CPC ............ *A61B 5/6821* (2013.01); *A61B 3/024* (2013.01); *A61B 3/102* (2013.01); *A61B 3/1241* (2013.01); *A61B 3/16* (2013.01); *A61B 3/18* (2013.01); *A61B 5/0095* (2013.01); *A61B 5/04842* (2013.01); *A61B 5/14542* (2013.01); *A61B 5/4041* (2013.01); *A61B 5/6843* (2013.01); *A61B 5/7246* (2013.01); *A61B 5/7278* (2013.01); *A61M 16/024* (2017.08); *A61M 16/1005* (2014.02); *A61B 2090/306* (2016.02); *A61B 2503/045* (2013.01); *A61B 2562/164* (2013.01); *A61B 2562/168* (2013.01); *A61B 2576/02* (2013.01); *A61M 2016/1025* (2013.01); *A61M 2205/3303* (2013.01)

(58) Field of Classification Search
None
See application file for complete search history.

(56) References Cited

U.S. PATENT DOCUMENTS

| 5,713,844 A | 2/1998 | Peyman |
| 7,549,752 B2 | 6/2009 | Peyman et al. |
| 7,828,440 B2 | 11/2010 | Peyman et al. |

(Continued)

*Primary Examiner* — Eric F Winakur
*Assistant Examiner* — Marjan Fardanesh
(74) *Attorney, Agent, or Firm* — The Law Office of Patrick F. O'Reilly III, LLC (57) ABSTRACT

A glaucoma testing device and a method of using the same are disclosed herein. The glaucoma testing device includes a device body portion having an outer housing and a flexible membrane at least partially defining a chamber supported within the outer housing; a fluid control system configured to insert an amount of the fluid into the chamber of the device body portion in order to expand the flexible membrane and exert pressure on an eye of a patient, or remove an amount of the fluid from the chamber of the device body portion in order to deflate the membrane and relieve pressure exerted on the eye; and a laser fiber optic configured to transmit a beam of light into the eye so as to produce a detectable ultrasonic wave so that an oxygenation level of the eye of the patient is capable of being determined using a photoacoustic system.

25 Claims, 6 Drawing Sheets

(51) Int. Cl.
*A61B 3/18* (2006.01)
*A61B 90/30* (2016.01)

(56) References Cited

U.S. PATENT DOCUMENTS

| | | | |
|---|---|---|---|
| 7,959,570 B2 | 6/2011 | Enikov et al. | |
| 8,121,663 B2 | 2/2012 | Peyman et al. | |
| 8,747,429 B2 * | 6/2014 | Peyman | A61F 9/00727 |
| | | | 128/898 |
| 10,133,056 B2 | 11/2018 | Peyman | |
| 10,278,920 B1 | 5/2019 | Peyman | |
| 2012/0150013 A1 * | 6/2012 | Peyman | A61B 5/0095 |
| | | | 600/407 |

* cited by examiner

GLAUCOMA TESTING DEVICE AND A METHOD USING THE SAME

CROSS-REFERENCE TO RELATED APPLICATIONS

This patent application claims priority to, and incorporates by reference in its entirety, U.S. Provisional Patent Application No. 62/408,653, entitled "Glaucoma Testing Device And A Method Using The Same", filed on Oct. 14, 2016.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a glaucoma testing device. More particularly, the invention relates to a device for performing a glaucoma stress test and for continuous monitoring of retinal and choroidal oxygenation, and to a method using the same.

2. Background

Glaucoma is a degenerative disease affecting optic, retinal ganglion cells, associated with a rise in intraocular pressure. In primary open-angle glaucoma (POAG), the anterior chamber angle is open. If the pressure is elevated without other glaucoma signs, it is called ocular hypertension. If the sign of glaucoma exists without increase in the intraocular pressure (IOP), it is called normotensive glaucoma. The cause of glaucoma could be variable, but vascular dysfunction leading to ischemia and optic nerve damage and the mechanical effect of increased IOP on the optic nerve head structure, which is called the cribriform plate, can also strangulate the retinal nerve fibers entering the nerve. However, optic nerve damage also can be caused by many other factors.

In general, an intraocular pressure (IOP) of about 20-21 mm Hg is considered normal with the absence of other symptoms. However, the diurnal variation of the intraocular pressure of 3-4 mm Hg can influence the results in the vulnerable eye. The IOP variation can occur almost hourly in patients (e.g. in the supine position). The diurnal variation can be higher in a glaucoma patient (e.g., increase in IOP up to 10 mm Hg or more at night and early morning), and cause significant damage to the optic nerve. The relationship of IOP and diastolic pressure can also have a negative effect on these patients at night when the diastolic pressure drops to a lower level. The visual signs of glaucoma are the cupping of the optic disc and the loss of the nerve fiber layer, along with the changes at the trabecular meshwork of the eye where the intraocular fluid is drained, which is also common in these patients. An imbalance between the IOP and intracranial pressure can also lead to gradual loss of visual field that can be constricted with time or completely lost, and the eye may become blind.

Despite the regular examination of glaucoma patients at a physician's office and therapy, many of the patients gradually lose their sight. Among the factors that have made the management of the glaucoma patients difficult is inability to measure the intraocular pressure (IOP) at night, and its influences on the retinal and optic nerve ischemia. Though recently some research has been performed to measure the IOP at night using a contact lens sensor placed on the cornea for 24 hours, this instrument at best provides minimal insight into the diurnal variation of the IOP. These lenses have to be prepared individually to fit each patient's corneal curvature. In addition they cannot be tolerated for more than 24 hours since they would deprive the cornea from the oxygen, and tear film lubrication, etc. leading to corneal abrasion. Also, they cannot give any other information, except for the indirect measurement of the IOP.

As such, presently there is no easy way to use an instrument to continuously measure the intraocular pressure (IOP) and oxygenation of the choroidal or retinal circulation over a 24 hour period or more, or to provide a controllable stress test as it exists in cardiology or in the diagnosis of diabetes, so as to provide a mean of variation of the blood flow/oxygenation that happens in normal or glaucoma patients due to the changes in the IOP.

The circadian variation of choroidal and retinal circulation as a result of the rise and drop of the intraocular pressure (IOP) has not been studied. In addition, there is no reliable instrument to controllably increase or decrease the intraocular pressure (IOP) for a period of time at the physician's office, or to create a stress test or simulate variation of the IOP in the eye and to measure simultaneously the physiological functional changes that an increase in IOP may cause on each individual patient, and more importantly in glaucoma patients.

Information on how glaucoma patents would recover after a rise in intraocular pressure (IOP) and how soon the recovery happens compared to normal patients is not available. It would be desirable to have an instrument that enables such a comparison to be made. Preferably, the instrument and the methodology employed using the instrument would not block or impair the physician's view inside the eye, and it would not block the patient's view to the outside world. Also, preferably, the instrument would still permit the simultaneous measurement of the IOP rise with the standard Goldmann tonometer. In addition, the instrument preferably would permit obtaining, during such an examination, that which would not be possible to do at night on the patient.

The aforedescribed known contact lens, which is used for the measurement of the intraocular pressure (IOP) for 24 hours, does not permit other important information to be determined from the eye. For example, the contact lens does not permit the increasing and decreasing of the IOP for a given pressure, and it does not permit numerous evaluations and tests to be performed. In particular, the contact lens does not permit obtaining information from the retina, choroid optic nerve head circulation, micro-vasculature, lamina cribrosa elasticity and its changes during a stress test, retinal circulation, axonal flow of the nerves, visual function of the patient such as visual acuity, visual field, using various source of stimulation of the retina, frequency doubling, automated perimetry or blue-yellow perimetry (SWAP), optical coherence tomography, optical coherence tomography angiography, blood flow measurement of the choroid and retinal circulation, electrophysiological tests, etc.

The treatment of glaucoma patients has been mostly medical by applying anti-glaucoma medication(s) as eye drops to reduce the intraocular pressure (IOP). However, at present, there is no means of evaluating what degree of reduction of IOP should occur. For example, it is unknown whether or not one should reduce the IOP to a normal level of 14-18 mm Hg. Although, there is no indication that this generalization is workable for each patient because there is no known way of stressing these eyes so as to find out what level of IOP rise these eyes can actually tolerate under the normal changes that occur daily in the IOP.

Known methods for the measurement of retinal oxygenation or choroidal oxygenation involve the use of experimental units. In general, these units are modified photography equipment for the back of the eye, the retina, and choroid optic nerve. These bulky instruments are uniformly located external to the body, and as with the fundus cameras, are equipped with numerous lenses through which a red or infrared light shines over a 2-3 mm diameter area of the retina under the operator's observation while the patient's pupil is dilated to make the fundus view possible. The degree of light absorbed during 1-2 minutes is measured by the degree of light reflected back to the camera, which records and analyzes the results. This unit requires the patient's cooperation and can give, at best, transient information on the blood oxygenation of a localized spot. The unit is not capable of measuring the retinal and choroidal circulation for any long period of time, and it does not provide a means of checking the effect of rise or fall of the intraocular pressure (IOP) in the eye of the patient. Also, it cannot also separate the retinal oxygenation from the choroidal oxygenation. It only produces a combination value of the both structures in a limited spot.

Therefore, it is apparent that a need exists for a glaucoma testing device and a method using the same that eliminates the shortcomings of the aforedescribed procedures.

BRIEF SUMMARY OF EMBODIMENTS OF THE INVENTION

Accordingly, the present invention is directed to a glaucoma testing device and a method of using the same that substantially obviates one or more problems resulting from the limitations and deficiencies of the related art.

In accordance with one or more embodiments of the present invention, there is provided a glaucoma testing device configured to be inserted under an eyelid of a patient. The glaucoma testing device includes a device body portion having an outer housing and a flexible membrane supported within the outer housing, the flexible membrane at least partially defining a chamber that receives a fluid therein; a fluid control system operatively coupled to the device body portion, the fluid control system configured to insert an amount of the fluid into the chamber of the device body portion in order to expand the flexible membrane and exert pressure on an eye of the patient, or remove an amount of the fluid from the chamber of the device body portion in order to deflate the membrane and relieve pressure exerted on the eye of the patient; and a laser fiber optic configured to transmit a beam of light into the eye of the patient, the beam of light configured to be absorbed by internal structures within the eye of the patient that produce a detectable ultrasonic wave when stimulated by the beam of light so that an oxygenation level of the eye of the patient is capable of being determined using a photoacoustic system.

In a further embodiment of the present invention, the photoacoustic system includes an ultrasonic receiver configured to detect the ultrasonic wave emitted from the internal structures within the eye of the patient, a photoacoustic imaging unit operatively coupled to the ultrasonic receiver, and a processor operatively coupled to the ultrasonic imaging unit, the processor configured to determine the oxygenation level of the eye based upon the ultrasonic wave received by the ultrasonic receiver.

In yet a further embodiment, the oxygenation level that is determined by the processor of the photoacoustic system is selected from the group consisting of the retinal oxygenation level, the choroidal oxygenation level, and combinations thereof.

In still a further embodiment, the ultrasonic wave has a frequency between approximately 0.5 MHz and approximately 10.0 MHz.

In yet a further embodiment, the amplitude of the ultrasonic wave is proportional to the oxygenation level of the eye.

In still a further embodiment, the processor of the photoacoustic system is operatively coupled to a gas delivery system for delivering oxygen to a patient, and wherein the amount of oxygen delivered to the patient is controlled based upon the oxygenation level of the eye determined by the photoacoustic system.

In yet a further embodiment, the device body portion comprises a flexible polymeric strip having a width between approximately 1.0 millimeter and approximately 2.0 millimeters, a length between approximately 4.0 millimeters and approximately 40.0 millimeters, and a thickness between approximately 0.1 millimeters and approximately 2.0 millimeters.

In still a further embodiment, the glaucoma testing device further comprises one or more pressure sensors disposed on a surface of the device body portion, the one or more pressure sensors configured to measure an intraocular pressure of the eye of the patient and output one or more signals based on the measured intraocular pressure of the eye, the one or more pressure sensors configured to wirelessly transmit the one or more signals to a processor located outside of the eye, and the processor configured to generate intraocular pressure data based upon the one or more signals outputted by the one or more pressure sensors.

In yet a further embodiment, the processor is located on an eyeglass frame of the patient, the processor configured to continuously generate the intraocular pressure data from the one or more signals transmitted by the one or more pressure sensors during a period of time selected from the group consisting of weeks, months, and years, and the processor is further configured to correlate the pressure data with the oxygenation level of the eye.

In still a further embodiment, the internal structures within the eye of the patient that are illuminated by the beam of light from the laser fiber optic are selected from the group consisting of the retina, the choroid, and combinations thereof.

In yet a further embodiment, the beam of light that is emitted from the laser fiber optic comprises infrared light or near-infrared light.

In still a further embodiment, the fluid control system comprises a micro-pump and a tube fluidly coupling the micro-pump to the chamber of the device body portion.

In accordance with one or more other embodiments of the present invention, there is provided a method of using a glaucoma testing device. The method comprising the steps of:

(i) providing a glaucoma testing device; (ii) inserting the device body portion of the glaucoma testing device underneath an eyelid of the patent in the conjunctival sulcus; (iii) delivering an amount of the fluid into the chamber of the device body portion of the glaucoma testing device in order to expand the flexible membrane and exert pressure on the eye of the patient;

(iv) transmitting a beam of light into the eye of the patient using the laser fiber optic; and (v) determining, by using the photoacoustic system, the oxygenation level of the eye of the patient from the ultrasonic wave generated from the internal structures within the eye stimulated by the beam of light. The glaucoma testing device includes a device body portion having an outer housing and a flexible membrane supported within the outer housing, the flexible membrane at least partially defining a chamber that receives a fluid therein; a fluid control system operatively coupled to the device body portion, the fluid control system configured to insert an amount of the fluid into the chamber of the device body portion in order to expand the flexible membrane and exert pressure on an eye of the patient, or remove an amount of the fluid from the chamber of the device body portion in order to deflate the membrane and relieve pressure exerted on the eye of the patient; and a laser fiber optic configured to transmit a beam of light into the eye of the patient, the beam of light configured to be absorbed by internal structures within the eye of the patient that produce a detectable ultrasonic wave when stimulated by the beam of light so that an oxygenation level of the eye of the patient is capable of being determined using a photoacoustic system.

In a further embodiment of the present invention, the oxygenation level of the eye of the patient is determined for a time period of greater than 24 hours.

In yet a further embodiment, the method further comprises the steps of: (vi) selectively increasing and decreasing the pressure exerted on the eye of the patient by inserting the fluid into, and withdrawing the fluid from the chamber of the device body portion of the glaucoma testing device so that the intraocular pressure of the eye of the patient varies over a period of time; and (vii) comparing the variations in the intraocular pressure of the eye of the patient over the period of time to variations in the intraocular pressure of one or more individuals of a normal population.

In still a further embodiment, the glaucoma testing device selectively increases and decreases the pressure exerted on the eye of the patient without obstructing the sight of the patient.

In yet a further embodiment, the step of determining the oxygenation level of the eye of the patient using the photoacoustic system comprises determining the retinal oxygenation level, the choroidal oxygenation level, and combinations thereof.

In still a further embodiment, the method further comprises the steps of:

(vi) measuring, by using a tonometer, the intraocular pressure of the eye of the patient; and (vii) determining a relationship between the amount of the fluid inserted into the chamber of the device body portion and a proportionate rise in the intraocular pressure of the eye of the patient as measured by the tonometer.

In yet a further embodiment, the step of determining the oxygenation level of the eye of the patient using the photoacoustic system comprises determining a retinal or choroidal oxygenation level before the intraocular pressure of the eye of the patient is increased using the glaucoma testing device, during an increase of the intraocular pressure of the eye of the patient using glaucoma testing device, after the intraocular pressure of the eye of the patient has been increased using glaucoma testing device, and immediately after the intraocular pressure of the eye of the patient returns to a base intraocular pressure.

In still a further embodiment, the step of delivering an amount of the fluid into the chamber of the device body portion of the glaucoma testing device comprises delivering an amount of fluid into the chamber of the device body portion that is sufficient to raise the intraocular pressure of the eye of the patient between approximately 25 mm Hg and approximately 40 mm Hg so that a retinal oxygenation level and choroidal oxygenation level are capable of being separately determined using the photoacoustic system.

In yet a further embodiment, the photoacoustic system includes an ultrasonic receiver configured to detect the ultrasonic wave emitted from the internal structures within the eye of the patient, a photoacoustic imaging unit operatively coupled to the ultrasonic receiver, and a processor operatively coupled to the ultrasonic imaging unit, the processor configured to determine the oxygenation level of the eye based upon the ultrasonic wave received by the ultrasonic receiver.

In still a further embodiment, the method further comprises the steps of:

(vi) positioning the ultrasonic receiver of the photoacoustic system above the eyebrow of the eye of the patient on the forehead skin of the patient; and (vii) detecting the ultrasonic wave emitted from the internal structures within the eye stimulated by the beam of light.

In yet a further embodiment, the method further comprises the step of: (vi) measuring, using the photoacoustic system, one or more additional visual parameters of the eye of the patient, the one or more additional visual parameters being measured using one of: frequency doubling, automated perimetry or blue-yellow perimetry (SWAP), optical coherence tomography, optical coherence tomography angiography, blood flow measurement of the choroid and retinal circulation, axonal glow of the retinal nerves, electrophysiological tests, and visual evoked response of the brain.

In still a further embodiment, the method further comprises the steps of:

(vi) measuring, using the photoacoustic system, a concentration of other analytes or other blood components of the serum by utilizing different wavelengths of visible or invisible light, the different wavelengths of light having wavelengths up to 1555 nanometers. In this further embodiment, an analyte concentration, such as glucose, etc., are measured by choosing a light in visible spectrum to the infrared frequencies of electromagnetic radiation up to a 1555 nanometer wavelength.

In yet a further embodiment, the glaucoma testing device further comprises one or more pressure sensors disposed on a surface of the device body portion, the one or more pressure sensors configured to measure an intraocular pressure of the eye of the patient and output one or more signals based on the measured intraocular pressure of the eye, the one or more pressure sensors configured to wirelessly transmit the one or more signals to a processor located outside of the eye, and the processor configured to generate intraocular pressure data based upon the one or more signals outputted by the one or more pressure sensors. Also, in this further embodiment, the method further comprises the steps of: (vi) measuring the intraocular pressure of the eye of the patient using the one or more pressure sensors; and (vii) simultaneously measuring retinal or choroidal physiological functions using the photoacoustic system while the intraocular pressure of the eye of the patient is measured using the one or more pressure sensors.

In still a further embodiment, the step of simultaneously measuring retinal or choroidal physiological functions using the photoacoustic system comprises simultaneously measuring retinal or choroidal oxygenation levels of the eye while the intraocular pressure of the eye of the patient is measured using the one or more pressure sensors. Also, in this further embodiment, the method further comprises the step of determining, by using the processor, a relationship between changes in the intraocular pressure of the eye of the patient and changes in the retinal or choroidal oxygenation levels of the eye of the patient.

In yet a further embodiment, the method further comprises the step of measuring, using the photoacoustic system, at least one of variations in blood flow, retinal or choroidal oxygenation levels, and other retinal and choroidal functions as a result of changes in the intraocular pressure of the eye of the patient.

In still a further embodiment, the method further comprises the steps of: (vi) measuring the intraocular pressure of the eye of the patient through the cornea, sclera, or lid of the eye; and (vii) determining a relationship between the amount of the fluid inserted into the chamber of the device body portion and a proportionate rise in the intraocular pressure of the eye of the patient as measured through the cornea, sclera, or lid of the eye.

In yet a further embodiment, the step of measuring the oxygenation level of the eye of the patient using the photoacoustic system comprises measuring the oxygenation level of the eye of a newborn infant so as to prevent excessive oxygen levels leading to retinopathy and inadequate oxygen levels leading to hypoxia.

In still a further embodiment, the step of measuring the oxygenation level of the eye of the patient using the photoacoustic system comprises measuring the oxygenation level of an ophthalmic artery, a branch of the carotid artery supplying blood to the brain, so as to estimate a brain oxygenation level of the patient.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 2:
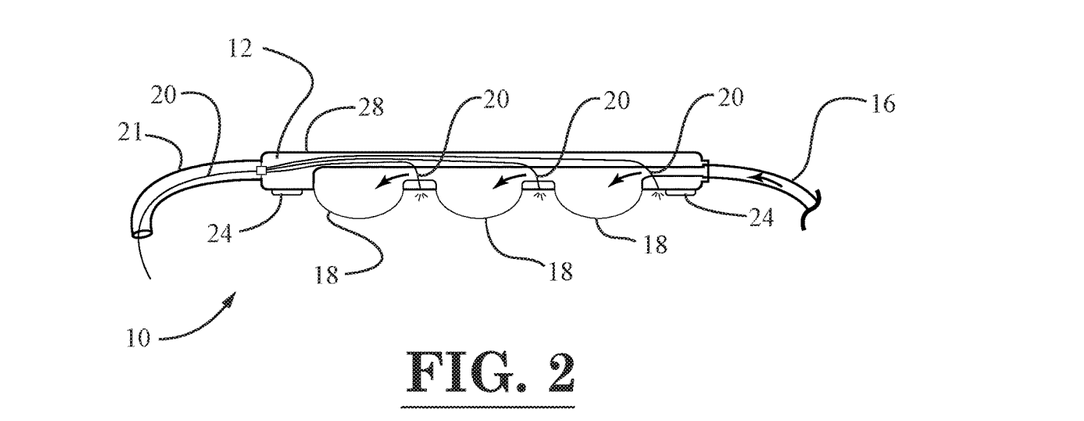
FIG. 2 is a top view of the glaucoma testing device of FIG. 1, wherein the membrane of the glaucoma testing device is shown in an inflated state as a result of fluid having been inserted into the chamber of the device.
Figure 3:
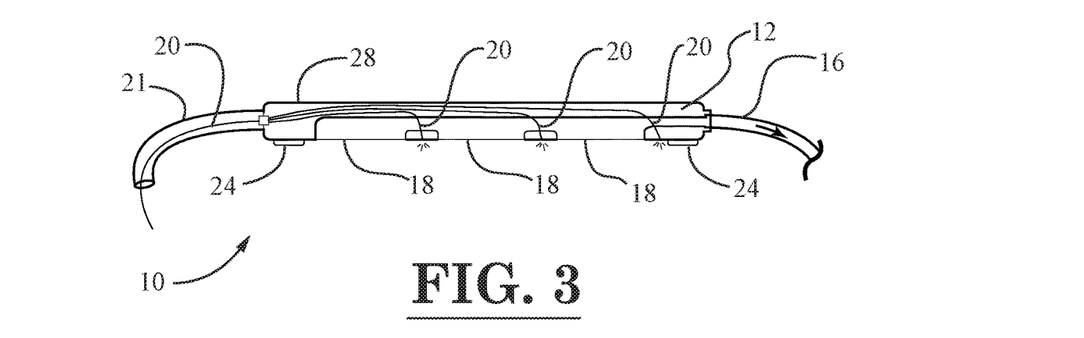
FIG. 3 is another top view of the glaucoma testing device of FIG. 1, wherein the membrane of the glaucoma testing device is shown in a deflated state as a result of fluid having been withdrawn from the chamber of the device, and wherein the pressure sensors of the device are illustrated thereon.
Figure 4:
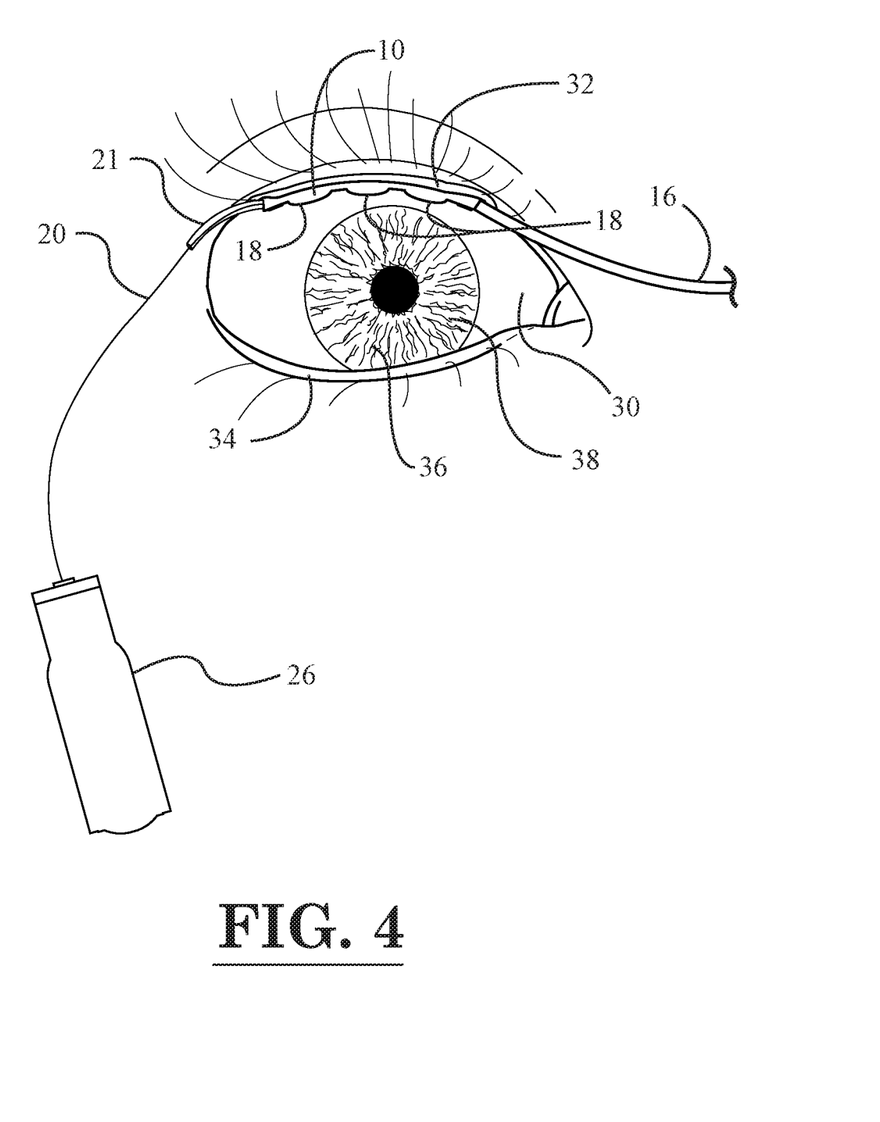
FIG. 4 is a front view of an eye, wherein the glaucoma testing device of FIG. 1 has been inserted under the eyelid of the eye in the conjunctival sulcus and a laser unit is shown connected to the glaucoma testing device.
Figure 5:
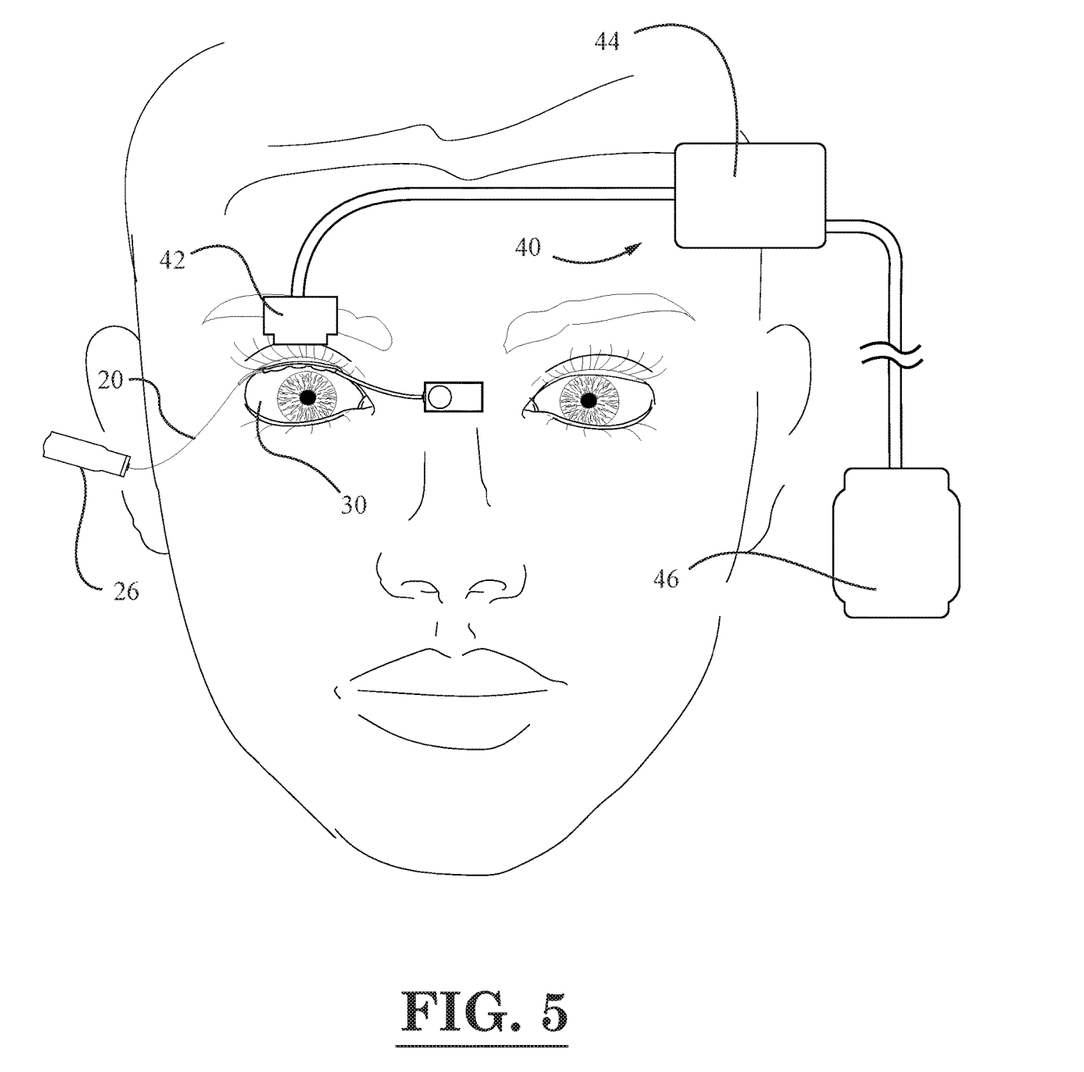
FIG. 5 is a diagrammatic view of a photoacoustic system utilized in conjunction with the glaucoma testing device of FIG. 1, wherein the ultrasonic receiver is shown disposed above the eye of the patient.

An illustrative embodiment of the glaucoma testing device is seen generally at 10 in FIGS. 1-4. As shown in these figures, in the illustrative embodiment, the glaucoma testing device 10 generally comprises a device body portion 12 having an outer housing 28 and a flexible membrane 18 supported within the outer housing 28, the flexible membrane 18 at least partially defining a chamber 14 that receives a fluid therein; a fluid control system (e.g., microfluidic control system 22) operatively coupled to the device body portion 12, the fluid control system 22 configured to insert an amount of the fluid into the chamber 14 of the device body portion 12 in order to expand the flexible membrane 18 and exert pressure on an eye of the patient, or remove an amount of the fluid from the chamber 14 of the device body portion 12 in order to deflate the membrane 18 and relieve pressure exerted on the eye of the patient; and a laser fiber optic 20 configured to transmit a beam of light into the eye of the patient, the beam of light configured to be absorbed by internal structures within the eye of the patient that produce a detectable ultrasonic wave when stimulated by the beam of light so that an oxygenation level of the eye of the patient is capable of being determined using a photoacoustic system 40 (as shown in FIG. 5). Referring to FIG. 4, it can be seen that the glaucoma testing device 10 may be inserted under an upper eyelid 32 in the conjunctiva sulcus of the eye 30 of a patient. In FIG. 4, the illustrated eye 30 of the patient further includes a lower eyelid 34, an iris 36, and a cornea 38. In addition, as shown in FIG. 4, the laser fiber optic 20 is connected to a laser generation unit 26 for generating the beam of light transmitted into the eye 30 of the patient. In the illustrative embodiment, the fibers of laser fiber optic 20 may be encased in a tube 21 (see FIGS. 1-4), or may be embedded inside a polymer block (e.g., a silicone block).

Figure 1:
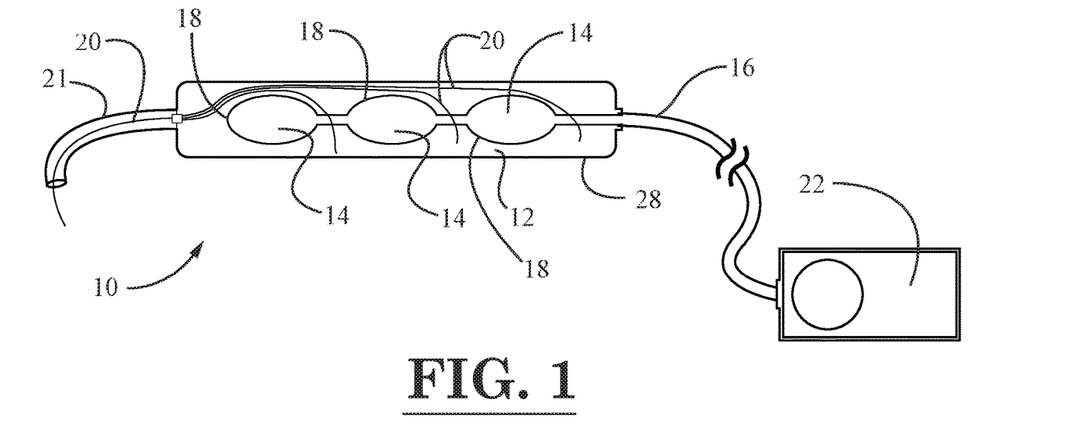
FIG. 1 is a rear view of a glaucoma testing device (i.e., facing the sclera when disposed in the eye), according to an embodiment of the invention.

With reference to FIGS. 1 and 2, in the illustrative embodiment, the glaucoma testing instrument or device 10 is connected to a tube 16 (i.e., microfluidic flexible cannula) that brings air or another fluid inside one or more chambers 14 located in the body 12 of the unit, thereby building a cavity which is covered from the outside with a thin, soft expendable membrane 18 that expands when the pressure of the fluid increases in the chamber 14. Also, in FIG. 1, it can be seen that the microfluidic control system 22, which may comprise a micro-pump, is fluidly coupled to the chamber 14 of the device body portion 12 of the glaucoma testing device 10 by the tube 16.

Turning to FIG. 3, it can be seen that the glaucoma testing device 10 may further comprise a plurality of pressure sensors 24 disposed on a surface of the device body portion 12. Each of the plurality of pressure sensors 24 is configured to measure an intraocular pressure of the eye of the patient and output one or more signals based on the measured intraocular pressure of the eye. In the illustrative embodiment, each of the pressure sensors 24 is configured to wirelessly transmit the one or more signals to a processor located outside of the eye (e.g., on an eyeglass frame of the patient). The processor is configured to generate intraocular pressure data based upon the one or more signals outputted by the plurality of pressure sensors 24.

Now, referring to FIG. 5, a photoacoustic system 40 utilized in conjunction with the glaucoma testing device 10 will be described. As shown in this figure, the photoacoustic system 40 includes an ultrasonic receiver 42 configured to detect the ultrasonic wave emitted from the internal structures within the eye 30 of the patient, a photoacoustic imaging unit 44 operatively coupled to the ultrasonic receiver 42, and a processor 46 operatively coupled to the ultrasonic imaging unit 44, the processor 46 configured to determine the oxygenation level of the eye based upon the ultrasonic wave received by the ultrasonic receiver 42. In one or more embodiments, the processor 46 of the photoacoustic system 40 is operatively coupled to a gas delivery system for delivering oxygen to a patient (e.g., a gas delivery system for infants). In these one or more embodiments, the amount of oxygen delivered to the patient is controlled based upon the oxygenation level of the eye determined by the photoacoustic system 40.

In an exemplary embodiment, the body portion 12 of the instrument 10 comprises a thin polymeric strip of a soft silicone or other polymer of 1-2 mm width or more, 4-40 mm long more or less, and 0.1 mm to a few mm thickness (see FIG. 1).

In the illustrative embodiment, as described above in conjunction with FIG. 3, the glaucoma testing instrument or device 10 includes a number of pressure sensors 24 on the surface of the unit facing the sclera to measure the intraocular pressure (IOP). The pressure sensors 24 are connected wirelessly to a processor outside the eye and record the pressure created on the eye, and then report the information wirelessly to a receiver outside the eye that is connected to the processor.

In one embodiment, the size of the glaucoma testing instrument or device 10 depends on the age and the size of the eye.

As shown in the illustrative embodiment of FIG. 4, the sterilized glaucoma testing instrument or device 10 is placed deep in the superior or inferior sulcus of the conjunctiva, under the lower or the upper lid or around the eye wall, so that it remains stably positioned.

Referring to FIGS. 1, 2, and 4, it can be seen that, in addition to the fluid channel and the expandable chamber 14, the glaucoma testing device or unit 10 is equipped with numerous 50 micron laser fiber optics 20 ending at the inferior part of the instrument 10, which come in close contact with the thin conjunctiva covering the sclera. After placement of the unit 10 on the sclera, the fiber optic 20 which is connected to diode laser unit 26 is able to send laser pulses to illuminate the choroid and retina with the light of a desired wavelength.

Figure 6:
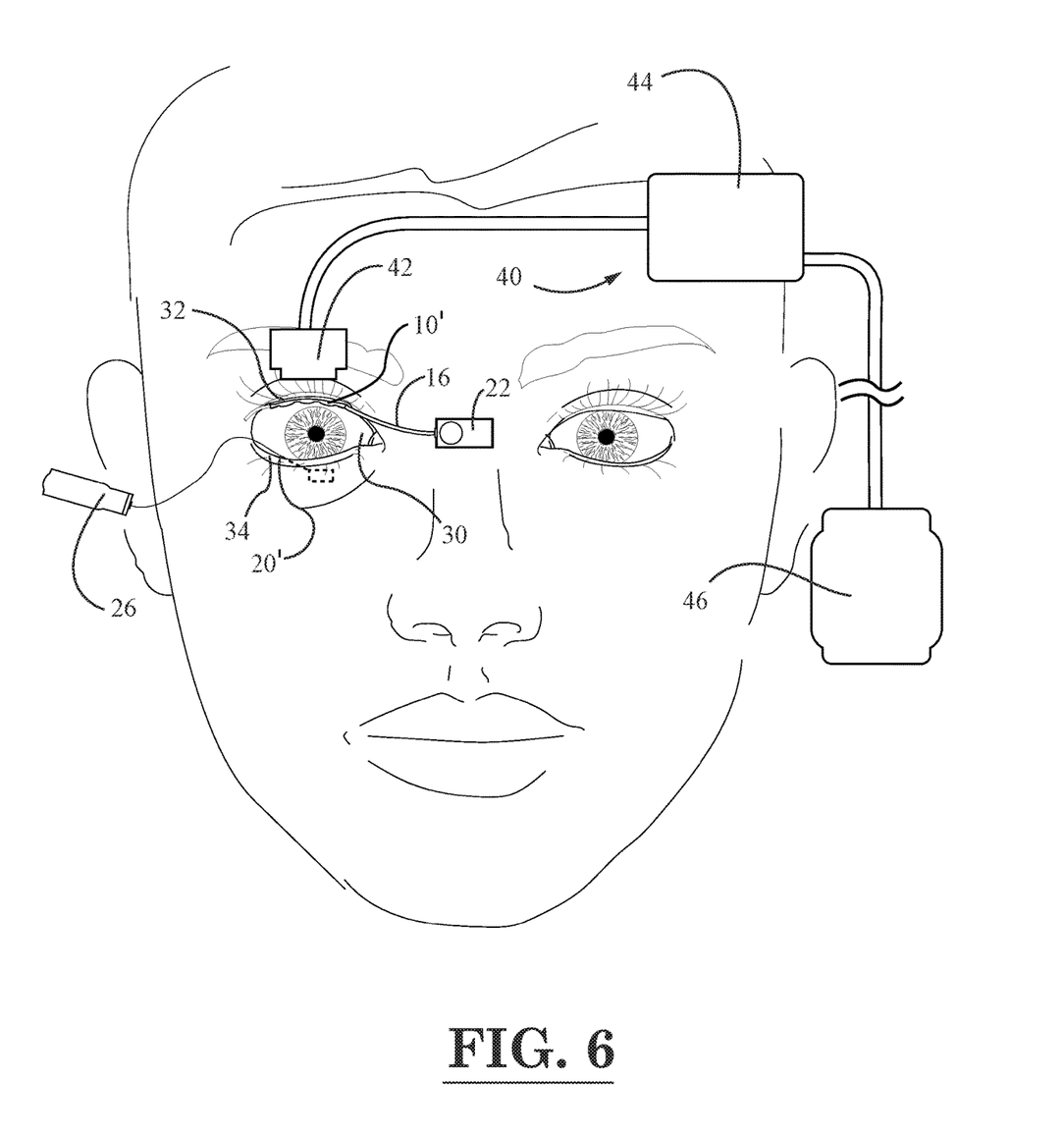
FIG. 6 is a diagrammatic view of a glaucoma testing device operatively coupled to a photoacoustic system, according to an alternative embodiment of the invention.

In an alternative embodiment, referring to FIG. 6, the IOP increasing unit (e.g., with the expandable chamber 14 and flexible membrane 18) of the device 10' is separated from the laser stimulating fiber 20', and photoacoustic sound and recording is obtained from another location of the eye to make it easier to implant the probe (e.g., in FIG. 6, the IOP increasing unit 10' is implanted under the upper lid 32 and the photoacoustic laser stimulating fibers 20' are implanted under the lower lid 34 in contact with the conjunctiva and sclera). Because the IOP increase in the eye occurs uniformly, the response will affect the retinal, choroid or optic nerve regardless of the position of the unit. As shown in FIG. 6, the processor 46 of the photoacoustic system 40 is operatively coupled to the laser generation unit 26 (i.e., the diode laser unit 26). Also, in FIG. 6, the ultrasonic imaging unit 44 of the photoacoustic system 40 is operatively coupled to the microfluidic control system 22 (e.g., a microprocessor coupled to micro-pump). As such, the systems are capable of interfacing with one another while simultaneously controllably regulating the intraocular pressure (IOP) of the eye 30 and measuring the oxygenation level of the eye 30 of the patient.

In the illustrative embodiment, near infrared light (NIR) or infrared (IR) light is used for stimulation because the sclera, choroid, and retina of the eye are transparent to near-infrared (NIR) light and infrared (IR) light. The combined thickness of the conjunctiva and sclera is about 0.5-0.7 mm at the eye's equator. Underneath the sclera lays a very rich vascular coat of the choroid of 0.2 mm thickness covering the entire posterior pole of the eye, followed by the 0.250-0.300 mm thick retinal layer, with its independent circulation forming the most interior part of the eye wall.

In the illustrative embodiment, by injecting fluid in the aforementioned device 10, the flexible membrane 18 bulges outward and exerts a defined pressure on the sclera depending on the amount of the fluid injected in the tube 16, which is the transmitted to the eye ball through the expanding membrane 18 of the chambers in the unit 10 so as to increase the IOP of the eye. By withdrawing the fluid, the pressure is reduced, and the pressure returns to its original normal intraocular pressure or less which is individualized.

In the illustrative embodiment, the degree of the fluid that is injected inside the chamber of the instrument is proportional to the amount of the rise in the IOP that is planned (e.g., a predetermined mm Hg rise per microliter), and it is measured simultaneously by the standard Goldmann tonometer contacting the corneal surface, and the information is stored in the unit's computer for future use and comparison.

In the illustrative embodiment, a Goldmann tonometer, or any other tonometer that is used clinically in every ophthalmic practice, may be utilized for the pressure measurements. By providing these measured pressure values to software of the aforedescribed unit wirelessly, the system provides an individualized profile of the degree of the pressure rise for each patient in mm Hg. As such, one can increase and decrease the IOP and hold it for the time desired for the study (e.g., 1-10 minutes, etc.). Preferably, the increase of the IOP is done gradually so that at all times the central retinal artery remains open.

In one embodiment, in astronauts, the unit is used to check the retinal oxygenation and other physiological functions in relationship with the IOP, or just measurement of the retinal or choroidal oxygenation, because these physiological parameters can increase or decrease for astronauts due to changes of the IOP, or simply due to an oxygen unit affecting blood oxygenation, without being noticeable by the astronauts. These changes of hyperoxia or hypoxia both have negative effects on the brain or heart, etc. leading to dementia or cardiovascular diseases, etc.

In one embodiment, this information is recorded for each patient in the processor and is accurate because, the injection unit can be directly connected to a micro-pump of the microfluidic control system 22 by which the relationship between the IOP rise and the amount of fluid are repeatable, and can be predictably reproduced for each patient and maintained in the patient's record.

In fact, because this is an easy procedure, in one embodiment, at each exam, the relationship can be examined easily and confirmed for the subsequent session used for physiological studies with a defined increase in the intraocular pressure (e.g., from 2 mm Hg to 10 mm Hg or more), and maintained for the duration of the study of 1 to 10 minutes, as required, depending on the patient's eye condition.

In one embodiment, all this information can be pre-planned and recorded and implemented via software present in the fluidic pump used for injection. The physiological function of the eye based on a given parameter (e.g., choroidal or retinal oxygenation, etc.) is measured before the start of the stress test, during and after the increase of the intraocular pressure (IOP), and immediately after the return to the patient's base IOP.

In one embodiment, the time to recovery of the physiological function to the pre-stressed eye will define how well the physiological function has normalized in each patient. In a diseased eye, the recovery time is statistically longer than the eye that does not have glaucoma. This means that a normal eye can tolerate the normal diurnal variation of the intraocular pressure (IOP) better than the eye which is compensated by the medication it receives.

In one embodiment, the instrument also provides means of separating retinal oxygenation from the choroidal oxygenation by increasing the intraocular pressure (IOP) beyond 25-40 mm Hg. At this level of the IOP, the choroidal circulation shuts off for a very short time period of less than a second, while the retinal circulation, which is a high flow system, is still open. A pulse of the laser, as described below, generates a photoacoustic sound, which is recorded by an ultrasonic receiver, placed above the eye brow on the patient's forehead skin. It is then converted to an electrical signal and further transmitted to the photoacoustic unit for analysis as PA spectroscopy (see FIG. 5).

In one embodiment, the amplitude of the photoacoustic (PA) sound wave correlates with the amount of oxygenated blood at a given level of pulse wave length, time degree of absorption by the oxyhemoglobin present either in the blood circulation (combined choroidal plus retinal circulation or just retinal circulation).

In one embodiment, the photoacoustic unit via its computer records all the testing information at each level of the intraocular pressure (IOP) for the duration of the test and beyond. Because the probe is located under the lid on the conjunctiva, it can remain in place 24 hours or longer as desired, without damaging the eye's structure. In addition, it is possible to use the photoacoustic (PA) system to measure the variation of the oxygenation during the phase of the circulation pulse of the eye choroid or retina separately.

In one embodiment, the diurnal variation of the blood oxygenation which is indirectly related to the variation of the intraocular pressure (IOP) change may be recorded by a processor placed and carried by the patient over the handle of a spectacle. The information on blood oxygenation may also be correlated with that obtained during the test to draw a conclusion on the fall and rise of the IOP at night, or measure the degree of hypoxia in patients with sleep apnea, in patients suffering from sleep disorder, or in cardiac patients, or patients with other diseases affecting blood oxygenation.

In one embodiment, by choosing the correct wavelength for oxy or reduced hemoglobin, one can separate oxygen level. The laser pulses of a wavelength of blue to infrared of 400-870 nm or near-infrared 670-870 nm are useful. Unfortunately, the absorption of these wavelengths by hemoglobin and oxyhemoglobin show overlapping absorption. However, the 900-1060 nm wavelengths absorption by reduced hemoglobin falls to the lowest level or zero, while that of oxyhemoglobin remains very strong, which increases the accuracy of the pure oxyhemoglobin measurement by photoacoustic (PA) technology.

In one embodiment, the light pulses can be generated by one or multiple small diode lasers that may be mounted on the spectacle frame that is carried by the patient. The diagnostic probe which is in contact with the sclera may also be equipped with one or a series or pressure sensors 24 that record the intraocular pressure (IOP) and its variation during the examination. This information may be simultaneously correlated with the blood oxygenation level and its variation measured by the Goldmann tonometer during the testing by the physician, and recorded. The data is stored in a small processor that can be used to create a graph of diurnal variation in blood oxygenation for the patient for 24 hours, or a given IOP variation.

In one embodiment, the glaucoma testing device or instrument 10 is able to measure a physiological parameter of the eye for a period of 24 hours or more (e.g., parameters, such as the oxygenation of the choroid and retina).

In one embodiment, the changes of the physiological function of the retina and choroid is simulated by controllably increasing or decreasing the intraocular pressure (IOP) and accurately measuring those changes and comparing those changes with those obtained from a normal population.

In one embodiment, the instrument raises and decreases controllably the intraocular pressure without obstructing the view inside the eye.

In one embodiment, the physiological function of the choroid and retina is measured before, during, and after the increase of intraocular pressure (IOP) using tests to obtain information from the retina, choroid optic nerve head circulation, micro-vasculature, lamina cribrosa elasticity and its changes during the stress test, retinal circulation, axonal flow of the nerves, visual function of the patient such as visual acuity, measurement photography, optical coherence tomography, optical coherence tomography angiography, blood flow measurement of the choroid and retinal circulation, visual field, using various source of stimulation of the retina, frequency doubling, automated perimetry or blue-yellow perimetry (SWAP), electrophysiological tests, measuring the brain electrical response, functional MRI response, and visual evoked response, etc.

In one embodiment, the test providing the information about the eye is obtained during the test from the retinal, choroid optic nerve, etc. to judge if the treatment or reduction of the intraocular pressure (IOP), or nerve protection has stabilized the condition of the choroid, retina and the optic nerve to significantly reduce the worsening of the disease, or whether the treatment has eliminated the disease.

In one embodiment, the instrument measures the retinal and choroidal oxygenation alone, or in combination, and the instrument records it for 24 hours or more to evaluate the diurnal variation that occurs so as to evaluate the abnormal tissue oxygenation caused by changes of the intraocular pressure (IOP), and potentially respiratory and neuronal origin.

In another embodiment, the unit utilizes photoacoustic technology applied directly to the eye to measure to measure retinal oxygenation, choroidal oxygenation, or optic nerve head oxygenation. Photoacoustic technology is based on light-stimulated expansion of a chromophore that absorbs that wavelength of light. The expansion of the molecule creates an ultrasound, which can be recorded by a receiver placed on the skin of the surrounding area.

In one embodiment, the photoacoustic sound wave has a frequency as low 0.5-10 MHz frequencies and passes with ease through the tissue including the bone. The sound waves are converted by piezoelectric compounds to electric pulses, which are amplified and transmitted to the photoacoustic unit and converted to 1 to 3 D images representing the amount of oxygenation of oxyhemoglobin depending on the wavelength of light that has been used.

In one embodiment, chronic measurement of oxygen level is useful also for newborn babies where too much oxygen can produce retinopathy of prematurity leading to blindness, and too low level can cause anoxia for these sensitive patients as prenatal hypoxia and its serious side effects. The sclera in a newborn is very thin 0.15 mm or less, and almost transparent, but it is transparent for the wavelength of 900-1000 nm or 1060 nm.

In one embodiment, the unit may also be used in a nursery for monitoring the premature infants to alarm the nurses if a dangerous level of oxygen, for the eye, has been reached, etc. Alternatively, the ophthalmic probe can be connected via a processor to the oxygen gas supplying unit to control the amount of the oxygen delivery to the patient automatically depending on the levels measured.

In one embodiment, this would eliminate the delay in the nurse's response, especially at night. There are many shortcomings in measuring the blood oxygenation from the superior sagittal sinus for the infants as was done in the past. Because the superior sagittal sinus is filled with the venous blood and not with arterial blood which carries oxygen. Therefore, it represents the oxygen left in reduced hemoglobin and not oxyhemoglobin. At the wavelength of 900-1000 nm or higher that the previous technology has used, it has measured the combination levels not purely the oxyhemoglobin. Therefore, the technology described herein is capable of improving the concept of measurement of brain oxygenation because the ophthalmic artery is a branch of the carotid artery supplying the brain with blood, and the retina in many respects represents the cellular structures present in the brain.

In addition, the photoacoustic (PA) spectroscopy unit may also be used to measure the retinal and choroidal circulation/blood flow, blood glucose, and other plasma analytes, etc. simultaneously because the probe is very close to the blood vessels of the retina and choroid, and the sclera is transparent for the infrared wavelength of light.

Figure 7:
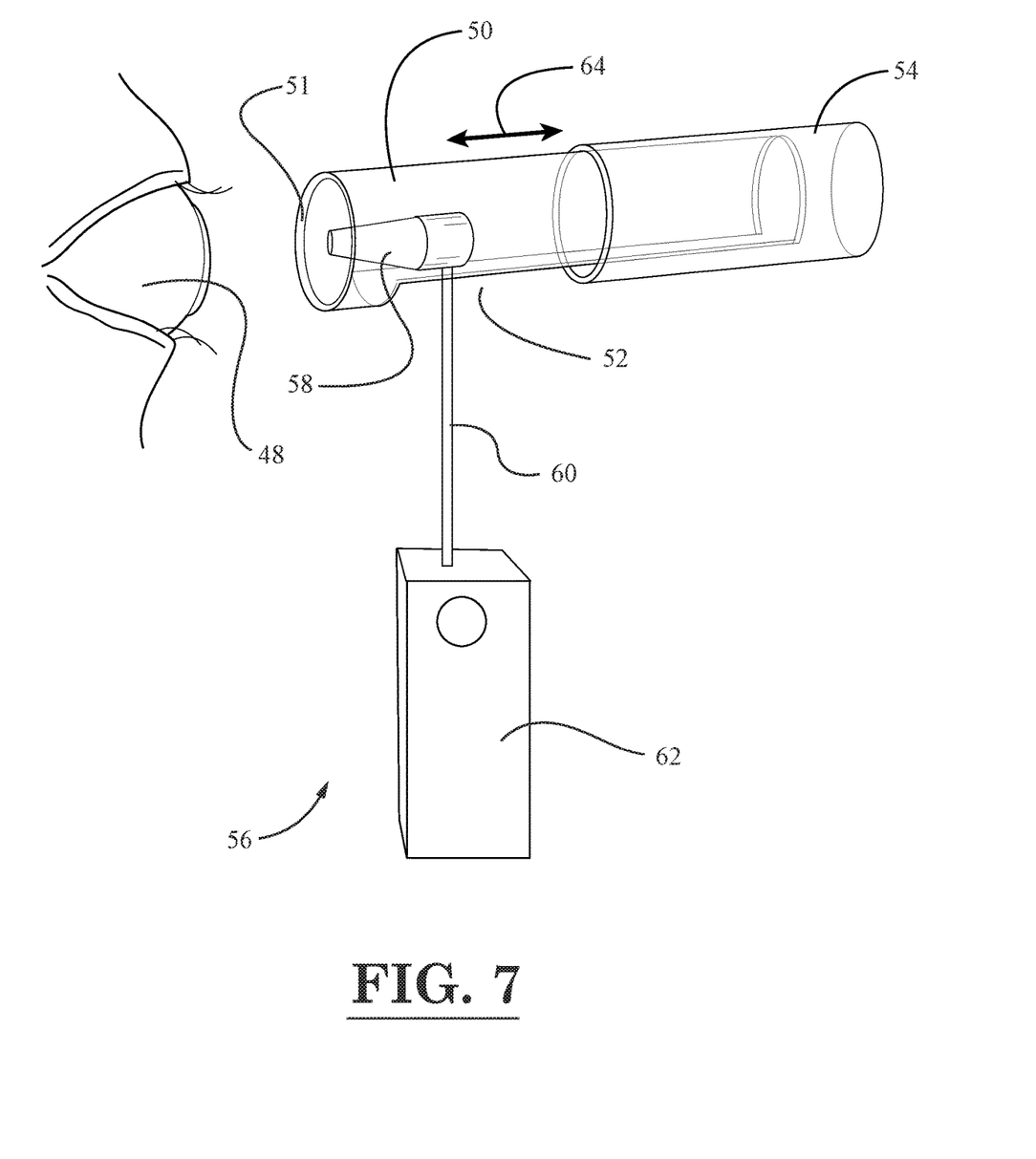
FIG. 7 is a side perspective view of another glaucoma testing device used for testing the intraocular pressure of an eye together with a Goldmann tonometer, according to an alternative embodiment of the invention.
Figure 8:
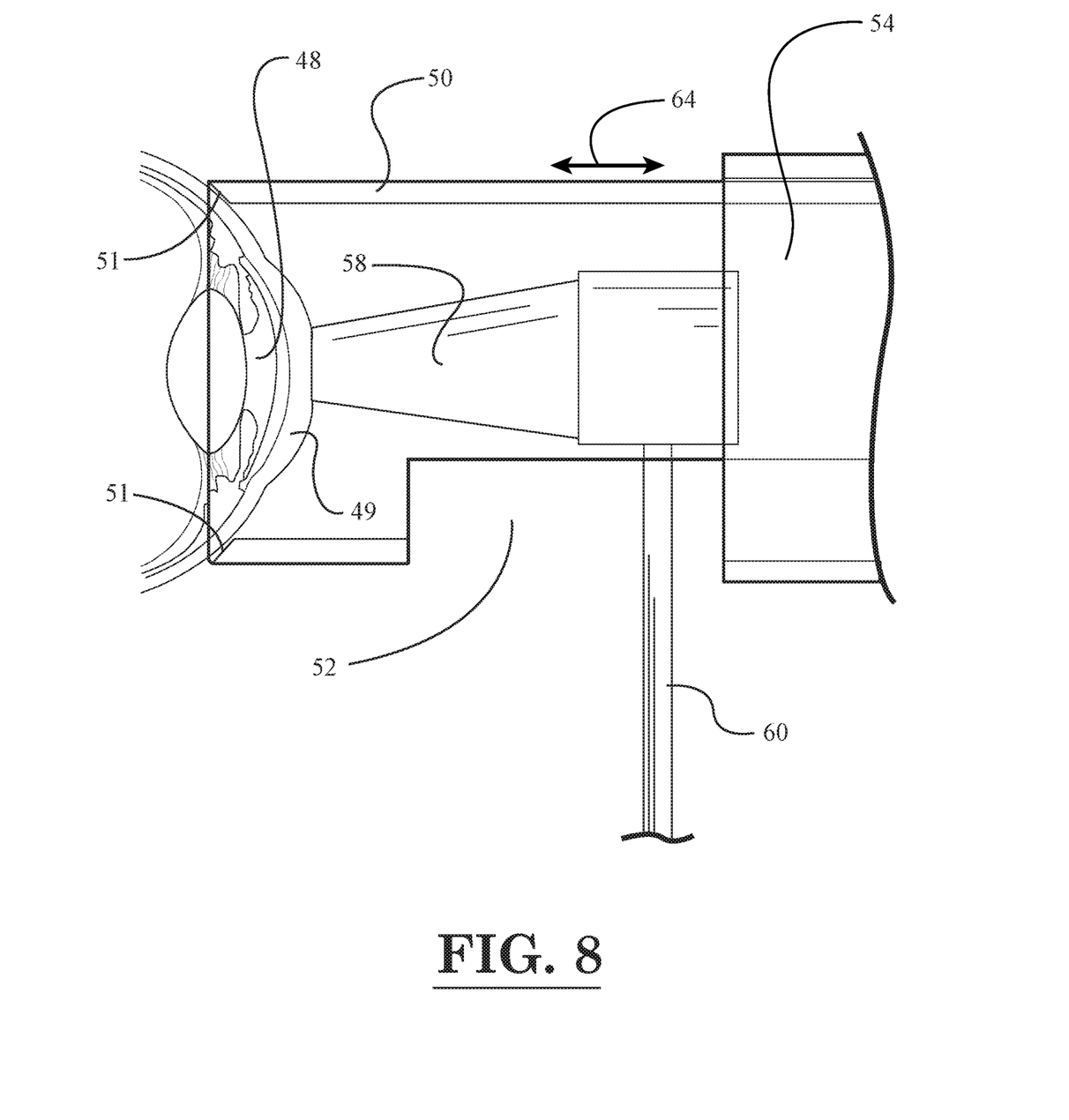
FIG. 8 is an enlarged side view illustrating the glaucoma testing device of FIG. 7 being pressed against the sclera of the eye, while the intraocular pressure of the eye is being measured using the Goldmann tonometer.

In another alternative embodiment, with reference to FIGS. 7 and 8, a tube-like instrument 50, 54 is used to controllably press against the sclera of an eye 48 to increase the intraocular pressure (IOP) of the eye 48 for a desired time while the IOP is measured separately using a Goldmann tonometer 56 (see FIGS. 7 and 8), an air puff pressure tonometer in a non-contact fashion, or any other IOP measurement means known in the art. As shown in FIG. 7, the Goldmann tonometer 56 has a prism portion 58 that is connected to the instrument body portion 62 by means of the arm 60. In this alternative embodiment, before increasing the IOP using the tube-like instrument 50, 54, the IOP is measured using the Goldmann tonometer 56. Then, the IOP is increased by 5-10 mmHg using the tube-like instrument 50, 54 and the IOP is measured again using the Goldmann tonometer 56. The changes that occur before, and after reducing the pressure by removing the instrument, are recorded. These changes, which may be a measurement of what happens to the posterior part of the eye, the retina, choroid, optic nerve, etc. may be determined using a regular standard fluorescein angiography, known OCT angiography, oximetry, or Doppler measurement of the blood flow in retinal, choroidal, or optic nerve capillaries, as described hereinbefore. The measured values may include the IOP rise while the IOP is raised, and the time for the eye to recover in those areas after pressure has returned to the pretest level. This measured time shows how long it takes for those parameters measured during the rise in the IOP to return to normal values of normal subjects of the same age. The longer the recovery time as compared to normal subjects, the greater chance of damage to the glaucomatous eye that is suffering from the increased IOP.

Now, referring again to FIGS. 7 and 8, the structure of the tube-like instrument 50, 54 will be described. Initially, as shown in FIG. 7, it can be seen that the instrument 50, 54 includes an inner tubular member 50 that is telescopically received within an outer tubular member 54. The outer tubular member 54 may be connected to a slit lamp camera, if desired. As diagrammatically indicated by the arrow 64 in FIG. 7, the inner tubular member 50 is configured to be selectively displaced by a user in a linear sliding manner relative to the outer tubular member 54 (i.e., the inner tubular member 50 may be displaced into the outer tubular member 54, or out of the outer tubular member 54). With combined reference to FIGS. 7 and 8, it can be seen that the bottom portion of the inner tubular member 50 is provided with an elongate slot or cutout 52 so as to enable the prism portion 58 of the Goldmann tonometer 56 to be inserted into the interior of the tubular member 50 (e.g., the wall of the inner tubular member 50 may extend 300 degrees, rather than 360 degrees, in the portion of the tubular member 50 comprising the slot 52). Rather than inserting the Goldmann tonometer 56 through the elongate slot or cutout 52 of the inner tubular member 50, an optical coherence tomography (OCT) device or a camera may also be inserted through the slot or cutout 52. Also, as illustrated in these figures, the end of the inner tubular member 50 that contacts the eye 48 is provided with a tapered edge 51 that is configured to be placed against the surface of the sclera of the eye 48. The edge 51 of the inner tubular member 50 is tapered so as to substantially correspond to the curvature of the eye 48. In the illustrative embodiment, the edge 51 of the inner tubular member 50 is in the form of a circular ring that contacts the sclera of the eye 48. In another alternative embodiment, the edge 51 of the inner tubular member 50 may be in the form of a semi-circular ring rather than a circular ring (e.g., if the elongate slot or cutout 52 extends completely to the end of the inner tubular member 50).

In the illustrative embodiment, turning to FIG. 8, when the edge 51 of the inner tubular member 50 is pressed against the scleral surface of the eye 48 so as to increase the intraocular pressure (IOP) of the eye 48, the Goldmann tonometer 56 is used to measure the IOP at the cornea 49 of the eye 48. Once the inner tubular member 50 is removed from the scleral surface of the eye 48, the IOP of the eye 48 returns to its original pressure (i.e., the pressure prior to being compressed by the inner tubular member 50). In FIG. 8, the Goldmann tonometer 56 touches the surface of the cornea 49 to measure the increase in the IOP.

Any of the procedures described herein can be used alone, or in conjunction with, simultaneously with, before or after any other procedure, method or device that would enhance the glaucoma testing of an eye of a patient. Additionally, any of the herein described embodiments can be used with any combination of the other embodiments.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A glaucoma testing device configured to be inserted under an eyelid of a patient, said glaucoma testing device comprising:
    a device body portion having an outer housing and a flexible membrane supported within the outer housing, the flexible membrane at least partially defining a chamber that receives a fluid therein;
    a fluid control system operatively coupled to the device body portion, the fluid control system configured to insert an amount of the fluid into the chamber of the device body portion in order to expand the flexible membrane and exert pressure on an eye of the patient, or remove an amount of the fluid from the chamber of the device body portion in order to deflate the membrane and relieve pressure exerted on the eye of the patient;
    a laser fiber optic configured to transmit a beam of light into the eye of the patient, the beam of light configured to be absorbed by internal structures within the eye of the patient that produce a detectable ultrasonic wave when stimulated by the beam of light so that an oxygenation level of the eye of the patient is capable of being determined using a photoacoustic system; and
    one or more pressure sensors disposed on a surface of the device body portion, the one or more pressure sensors configured to measure an intraocular pressure of the eye of the patient and output one or more signals based on the measured intraocular pressure of the eye, the one or more pressure sensors configured to transmit the one or more signals to a processor located outside of the eye, and the processor configured to generate intraocular pressure data based upon the one or more signals outputted by the one or more pressure sensors.

2. The glaucoma testing device according to claim 1, wherein the photoacoustic system includes an ultrasonic receiver configured to detect the ultrasonic wave emitted from the internal structures within the eye of the patient, a photoacoustic imaging unit operatively coupled to the ultrasonic receiver, and a photoacoustic processor operatively coupled to the photoacoustic imaging unit, the photoacoustic processor configured to determine the oxygenation level of the eye based upon the ultrasonic wave received by the ultrasonic receiver, wherein the oxygenation level that is determined by the photoacoustic processor of the photoacoustic system is selected from the group consisting of the retinal oxygenation level, the choroidal oxygenation level, and combinations thereof.

3. The glaucoma testing device according to claim 2, wherein the ultrasonic wave has a frequency between approximately 0.5 MHz and approximately 10.0 MHz, and wherein the amplitude of the ultrasonic wave is proportional to the oxygenation level of the eye.

4. The glaucoma testing device according to claim 2, wherein the photoacoustic processor of the photoacoustic system is operatively coupled to a gas delivery system for delivering oxygen to a patient, and wherein the amount of oxygen delivered to the patient is controlled based upon the oxygenation level of the eye determined by the photoacoustic system.

5. The glaucoma testing device according to claim 1, wherein the device body portion comprises a flexible polymeric strip having a width between approximately 1.0 millimeter and approximately 2.0 millimeters, a length between approximately 4.0 millimeters and approximately 40.0 millimeters, and a thickness between approximately 0.1 millimeters and approximately 2.0 millimeters.

6. The glaucoma testing device according to claim 1, wherein the one or more pressure sensors are configured to wirelessly transmit the one or more signals to the processor, and wherein the processor is located on an eyeglass frame of the patient, the processor configured to continuously generate the intraocular pressure data from the one or more signals transmitted by the one or more pressure sensors during a period of time selected from the group consisting of weeks, months, and years, and the processor further configured to correlate the pressure data with the oxygenation level of the eye.

7. The glaucoma testing device according to claim 1, wherein the internal structures within the eye of the patient that are illuminated by the beam of light from the laser fiber optic are selected from the group consisting of the retina, the choroid, and combinations thereof.

8. The glaucoma testing device according to claim 1, wherein the beam of light that is emitted from the laser fiber optic comprises infrared light or near-infrared light.

9. The glaucoma testing device according to claim 1, wherein the fluid control system comprises a micro-pump and a tube fluidly coupling the micro-pump to the chamber of the device body portion.

10. A method of using a glaucoma testing device, said method comprising the steps of:
    providing a glaucoma testing device that includes:
        a device body portion having an outer housing and a flexible membrane supported within the outer housing, the flexible membrane at least partially defining a chamber that receives a fluid therein;
        a fluid control system operatively coupled to the device body portion, the fluid control system configured to insert an amount of the fluid into the chamber of the device body portion in order to expand the flexible membrane and exert pressure on an eye of the patient, or remove an amount of the fluid from the chamber of the device body portion in order to deflate the membrane and relieve pressure exerted on the eye of the patient;
        a laser fiber optic configured to transmit a beam of light into the eye of the patient, the beam of light configured to be absorbed by internal structures within the eye of the patient that produce a detectable ultrasonic wave when stimulated by the beam of light so that an oxygenation level of the eye of the patient is capable of being determined using a photoacoustic system; and one or more pressure sensors disposed on a surface of the device body portion, the one or more pressure sensors configured to measure an intraocular pressure of the eye of the patient and output one or more signals based on the measured intraocular pressure of the eye, the one or more pressure sensors configured to transmit the one or more signals to a processor located outside of the eye, and the processor configured to generate intraocular pressure data based upon the one or more signals outputted by the one or more pressure sensors;

inserting the device body portion of the glaucoma testing device underneath an eyelid of the patent in the conjunctival sulcus;

delivering an amount of the fluid into the chamber of the device body portion of the glaucoma testing device in order to expand the flexible membrane and exert pressure on the eye of the patient;

measuring the intraocular pressure of the eye of the patient using the one or more pressure sensors;

transmitting a beam of light into the eye of the patient using the laser fiber optic; and determining, by using the photoacoustic system, the oxygenation level of the eye of the patient from the ultrasonic wave generated from the internal structures within the eye stimulated by the beam of light.

11. The method according to claim 10, wherein the oxygenation level of the eye of the patient is determined for a time period of greater than 24 hours.

12. The method according to claim 10, further comprising the steps of:

selectively increasing and decreasing the pressure exerted on the eye of the patient by inserting the fluid into, and withdrawing the fluid from the chamber of the device body portion of the glaucoma testing device so that the intraocular pressure of the eye of the patient varies over a period of time; and comparing the variations in the intraocular pressure of the eye of the patient over the period of time to variations in the intraocular pressure of one or more individuals of a normal population;

wherein the glaucoma testing device selectively increases and decreases the pressure exerted on the eye of the patient without obstructing the sight of the patient.

13. The method according to claim 10, wherein the step of determining the oxygenation level of the eye of the patient using the photoacoustic system comprises determining the retinal oxygenation level, the choroidal oxygenation level, and combinations thereof.

14. The method according to claim 10, further comprising the steps of:

measuring, by using a tonometer, the intraocular pressure of the eye of the patient; and determining a relationship between the amount of the fluid inserted into the chamber of the device body portion and a proportionate rise in the intraocular pressure of the eye of the patient as measured by the tonometer.

15. The method according to claim 10, wherein the step of determining the oxygenation level of the eye of the patient using the photoacoustic system comprises determining a retinal or choroidal oxygenation level before the intraocular pressure of the eye of the patient is increased using the glaucoma testing device, during an increase of the intraocular pressure of the eye of the patient using glaucoma testing device, after the intraocular pressure of the eye of the patient has been increased using glaucoma testing device, and immediately after the intraocular pressure of the eye of the patient returns to a base intraocular pressure.

16. The method according to claim 10, wherein the step of delivering an amount of the fluid into the chamber of the device body portion of the glaucoma testing device comprises delivering an amount of fluid into the chamber of the device body portion that is sufficient to raise the intraocular pressure of the eye of the patient between approximately 25 mm Hg and approximately 40 mm Hg so that a retinal oxygenation level and choroidal oxygenation level are capable of being separately determined using the photoacoustic system.

17. The method according to claim 10, wherein the photoacoustic system includes an ultrasonic receiver configured to detect the ultrasonic wave emitted from the internal structures within the eye of the patient, a photoacoustic imaging unit operatively coupled to the ultrasonic receiver, and a photoacoustic processor operatively coupled to the photoacoustic imaging unit, the photoacoustic processor configured to determine the oxygenation level of the eye based upon the ultrasonic wave received by the ultrasonic receiver; and wherein the method further comprises the steps of:

positioning the ultrasonic receiver of the photoacoustic system above the eyebrow of the eye of the patient on the forehead skin of the patient; and detecting the ultrasonic wave emitted from the internal structures within the eye stimulated by the beam of light.

18. The method according to claim 10, further comprising the step of:

measuring, using the photoacoustic system, one or more additional visual parameters of the eye of the patient, the one or more additional visual parameters being measured using one of: frequency doubling, automated perimetry or blue-yellow perimetry (SWAP), optical coherence tomography, optical coherence tomography angiography, blood flow measurement of the choroid and retinal circulation, axonal glow of the retinal nerves, electrophysiological tests, and visual evoked response of the brain.

19. The method according to claim 10, further comprising the step of:

measuring, using the photoacoustic system, a concentration of other analytes or other blood components of the serum by utilizing different wavelengths of visible or invisible light, the different wavelengths of light having wavelengths up to 1555 nanometers.

20. The method according to claim 10, wherein the one or more pressure sensors are configured to wirelessly transmit the one or more signals to the processor located outside of the eye; and the method further comprises the step of:

simultaneously measuring retinal or choroidal physiological functions using the photoacoustic system while the intraocular pressure of the eye of the patient is measured using the one or more pressure sensors.

21. The method according to claim 20, wherein the step of simultaneously measuring retinal or choroidal physiological functions using the photoacoustic system comprises simultaneously measuring retinal or choroidal oxygenation levels of the eye while the intraocular pressure of the eye of the patient is measured using the one or more pressure sensors; and the method further comprises the step of:

determining, by using the processor, a relationship between changes in the intraocular pressure of the eye of the patient and changes in the retinal or choroidal oxygenation levels of the eye of the patient.

22. The method according to claim 10, further comprising the step of:
measuring, using the photoacoustic system, at least one of variations in blood flow, retinal or choroidal oxygenation levels, and other retinal and choroidal functions as a result of changes in the intraocular pressure of the eye of the patient.

23. The method according to claim 10, wherein the step of measuring the intraocular pressure of the eye of the patient further comprises measuring the intraocular pressure of the eye of the patient through the cornea, sclera, or lid of the eye, and the method further comprises the step of:
determining a relationship between the amount of the fluid inserted into the chamber of the device body portion and a proportionate rise in the intraocular pressure of the eye of the patient as measured through the cornea, sclera, or lid of the eye.

24. The method according to claim 10, wherein the step of measuring the oxygenation level of the eye of the patient using the photoacoustic system comprises measuring the oxygenation level of the eye of a newborn infant so as to prevent excessive oxygen levels leading to retinopathy and inadequate oxygen levels leading to hypoxia.

25. The method according to claim 10, wherein the step of measuring the oxygenation level of the eye of the patient using the photoacoustic system comprises measuring the oxygenation level of an ophthalmic artery, a branch of the carotid artery supplying blood to the brain, so as to estimate a brain oxygenation level of the patient.

* * * * *